US009773312B2

(12) United States Patent
Lee

(10) Patent No.: US 9,773,312 B2
(45) Date of Patent: Sep. 26, 2017

(54) METHOD OF REGISTRATING A CAMERA OF A SURGICAL NAVIGATION SYSTEM FOR AN AUGMENTED REALITY

(71) Applicant: KOH YOUNG TECHNOLOGY INC., Seoul (KR)

(72) Inventor: Hyun-Ki Lee, Daegu (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 0 days.

(21) Appl. No.: 14/402,370

(22) PCT Filed: May 27, 2013

(86) PCT No.: PCT/KR2013/004594
§ 371 (c)(1),
(2) Date: Nov. 20, 2014

(87) PCT Pub. No.: WO2013/176525
PCT Pub. Date: Nov. 28, 2013

(65) Prior Publication Data
US 2015/0109458 A1   Apr. 23, 2015

(30) Foreign Application Priority Data

May 25, 2012  (KR) .................. 10-2012-0055913
May 27, 2013  (KR) .................. 10-2013-0059435

(51) Int. Cl.
*G06T 7/00*   (2017.01)
*G06T 7/80*   (2017.01)
(Continued)

(52) U.S. Cl.
CPC .............. *G06T 7/0018* (2013.01); *G06T 7/74* (2017.01); *G06T 7/80* (2017.01);
(Continued)

(58) Field of Classification Search
CPC .................. G06T 19/00; G06T 19/006; G06T 2207/30204; G06T 2207/30208;
(Continued)

(56) References Cited

U.S. PATENT DOCUMENTS

| 2008/0097156 A1* | 4/2008 | Nakamura ............. A61B 1/045 600/117 |
| 2010/0134688 A1* | 6/2010 | Moriwake .......... G06K 9/00228 348/586 |
| 2010/0165116 A1* | 7/2010 | Hsieh ........................ G06T 7/73 348/187 |

FOREIGN PATENT DOCUMENTS

| JP | 2010-287174 | 12/2010 |
| JP | 2011-224266 | 11/2011 |

(Continued)

OTHER PUBLICATIONS

Donnici et al., "An Algorithm to Implement a Fluoroscopic Stereo System using a Single Simulated Fluoroscope and an Optical Navigator," World Scientific and Engineering Academy and Society WSEAS, Jan. 25, 2012, pp. 212-216.*

(Continued)

*Primary Examiner* — Kenny Cese
(74) *Attorney, Agent, or Firm* — Kile Park Reed & Houtteman PLLC

(57) ABSTRACT

A method of registering a camera of a surgical navigation system for an augmented reality which realizes an augmented reality with lowered error range is disclosed. The method of registering the camera of the surgical navigation system for the augmented reality enables single person to do the work by calculating and adjusting the coordinate of the optical center of the camera by moving the optical tracker, the camera, or the pattern board with a second marker attached on the pattern board, not manually attached on the pattern board. And, there is an effect of improving accuracy (Continued)

and safety of a surgery by realizing an augmented reality without generating an accumulated error by the second marker, since the spatial coordinate of the second marker attached on the pattern board maintains uniform.

11 Claims, 11 Drawing Sheets

(51) Int. Cl.
  *G06T 7/73* (2017.01)
  *A61B 17/00* (2006.01)
  *A61B 34/20* (2016.01)
  *A61B 90/00* (2016.01)

(52) U.S. Cl.
  CPC .............. *A61B 2017/00725* (2013.01); *A61B 2034/2055* (2016.02); *A61B 2034/2065* (2016.02); *A61B 2090/365* (2016.02); *G06T 2207/30204* (2013.01); *G06T 2207/30244* (2013.01)

(58) Field of Classification Search
  CPC ..... G06T 7/0018; G06T 17/00; G06T 7/0044; G06T 2207/30244; G06T 7/80; G06T 7/74; A61B 2034/2055; A61B 2017/00725; A61B 2034/2065; A61B 2090/3983
  See application file for complete search history.

(56) References Cited

FOREIGN PATENT DOCUMENTS

| KR | 10-2007-0050878 | 5/2007 |
| KR | 10-2011-0006360 | 1/2011 |

OTHER PUBLICATIONS

Duan, "3D Tracking and Positioning of Surgical Instruments in Virtual Surgery Simulation," Dec. 2011, Journal of Multimedia,vol. 6, No. 6.*
Jing et al., "The Improvement of Automatic Identification method based on Circular Markers," Jan. 2012, Article in Electronic Journal of Geotechnical Engineering 17:2943-2948.*
Ma et al., "An Invitation to 3-D Vision from Images to Models," Nov. 19, 2001.*
Zhang, "A Flexible New Technique for Camera Calibration," 1999, IEEE.*
Zhang, "A flexible new technique for camera calibration", 2000, IEEE Transactions on Pattern Analysis and Machine Intelligence, 22(11), pp. 1330-1334.*
Jing et al. "The Improvement of Automatic Identification method based on Circular Markers," Jan. 2012, Article in Electronic Journal of Geotechnical Engineering 17: 2943-2948.*
Zhang, "A flexible new technique for camera calibration", 2000, IEEE Transactions on Pattern Analysis and Machine Intelligence, 22(1), pp. 1330-1334.*
Written Opinion of the International Searching Authority for International Application No. PCT/KR2013/004594, dated Apr. 9, 2013.
International Search Report for International Application No. PCT/KR2013/004594, dated Sep. 4, 2013.

* cited by examiner

130

METHOD OF REGISTRATING A CAMERA OF A SURGICAL NAVIGATION SYSTEM FOR AN AUGMENTED REALITY

TECHNICAL FIELD

The present invention relates to a method of registering a camera of a surgical navigation system for an augmented reality, and more particularly to a method of registering a camera of a surgical navigation system for an augmented reality, which may adjust spatial coordinates between an optical center of a camera and a marker attached on a camera.

BACKGROUND ART

Augmented reality is a technology by which computer graphic (CG) made by computer coexists with a real world to enable users to feel like the computer graphic exists in the real world. In augmented reality, virtual environment made by a computer is used to supplement the real world with a virtual world, but the main part is the real environment. In other words, it provides information required for the real environment by overlapping 3-dimensional images with a real image the user is watching.

Meanwhile, a degree of accuracy is required for medical operation of a doctor on a patient and the doctor is required to be capable of monitoring the current status during surgery. Especially in case of brain surgery, it is necessary to actively secure sight of seeing the surgeon wishes, but the current surgical system is not enough to solve to this problem.

A navigation system and the like, thus, are used for solving this problem. While the conventional surgical method relies on doctor's experiences, the navigation surgery is highly accurate because it has undergone a verification procedure through a computer.

However, the navigation system cannot achieve effective display alone. In other words, most of obtained images are 2-dimensional images which require lots of experiences and judgments of doctors, and such information which relies on operator's imagination may cause mistakes or difficulty in accurate operation.

Recently, thus, in order to improve operation accuracy, augmented reality that displays patient's image like CT (computer tomography) or MRI (magnetic resonance imaging) with being overlapped with image captured by camera is applied to the navigation system.

In this case, the more accurate augmented reality can be achieved only when adjustment of coordinate of an optical center of the camera is done.

FIG. 1 is a diagram explaining the conventional method of adjusting coordinate of an optical center of a camera.

Referring to FIG. 1, for adjusting the optical center of the camera 120, after the operator manually stamped a tool to which the marker 140 is attached on a pattern board 130, it is performed to track the marker 140 attached on the camera 120 and the marker 140 attached on the tool via optical tracker 110 of the navigation system to detect a coordinate $O_{pp}$ of the marker 140 attached on the camera 120 and a coordinate $O_{pp}$ of the marker 140 attached on the tool. Then, a coordinate $O_c$ of an optical center of the camera 120 is calculated by using the coordinate $O_{pp}$ of the marker 140 attached on the camera 120 and the coordinate $O_{cm}$ of the marker 140 attached on the tool, and a position and an orientation of the optical center of the camera is adjusted by a processor (not shown).

However, as described above, the conventional method of calculating a distance between an optical center of a camera 120 has a problem that an error range of an augmented reality becomes bigger since a coordinate $O_{pp}$ of a marker 140 attached on a tool is calculated by manually stamping the tool, which is attached on the marker 140, on a pattern board 130.

In other words, an error range of an augmented reality is large since it is not possible to stamp accurately every time a tool, on which a marker 140 is attached, on the pattern board 130 to a coordinate system direction by manually, and as well as, an error range of an augmented reality becomes larger since an error is accumulated by calculating a spatial coordinate of a marker 140 according to each position of a tool on which the marker 140 is attached, the maker 140 is attached on the tool stamped on a pattern board several times with different positions.

In addition, since the tool is manually stamped on the pattern board 130, therefore, single person is impossible to do the work.

DETAILED DESCRIPTION OF THE INVENTION

Objects of the Invention

Therefore, the present invention is to solve the above-described problem, the object of the present invention is to provide a method of registering a camera for surgical navigation system which realizes an augmented reality with lowered error range.

Technical Solution

A method of registering a camera of a surgical navigation system for an augmented reality according to an embodiment of the present invention comprises a first step of, by a processor, finding spatial coordinates of first and second markers from a spatial coordinate of an optical tracker, calculating a spatial coordinate of an origin of a pattern board from a spatial coordinate of an optical center of a camera, and storing the calculated coordinates in the processor, when the spatial coordinates of the first and second markers have been changed multiple times, which are attached on the camera and the pattern board, respectively, and tracked by the optical tracker, and a second step of adjusting, by the processor, the spatial coordinate of the optical center of the camera by using the spatial coordinates of the first marker and second marker from the spatial coordinate of the optical tracker and the spatial coordinate of the origin of the pattern board from the spatial coordinate of an optical center of the camera, and storing the adjusted spatial coordinate in the processor.

In one embodiment, the second marker is attached on a portion of the pattern board on which a pattern is formed.

In another embodiment, the second marker is attached on a portion of the pattern board on which a pattern is not formed.

In one embodiment, a chess pattern or a circular pattern is formed on the pattern board.

In one embodiment, the first step comprises finding, by the processor, the spatial coordinates of the first and second markers through the processor from the spatial coordinate of the optical tracker by tracking the first and second markers by the optical tracker, calculating, by the processor, the spatial coordinate of the origin of the pattern board from the spatial coordinate of the optical center of the camera by using an image of a check board obtained by the camera, and changing multiple times the spatial coordinates of the first and second markers from the spatial coordinate of the optical tracker and performing each time the step of finding the spatial coordinates and the step of calculating the spatial coordinates, and finding each spatial coordinate of the first and second markers from the spatial coordinate of the optical tracker and each spatial coordinate of the origin of the pattern board from the spatial coordinate of the optical center of the camera.

Meanwhile, calculating the spatial coordinate of the origin of the pattern board comprises capturing, by the camera, an image of the pattern board, transmitting the captured image of the pattern board obtained from the camera to the processor, calculating, by the processor, the spatial coordinate of the origin of the pattern board from the spatial coordinate of the optical center of the camera through adjusting the camera by using the captured image of the pattern board.

In one embodiment, it may be preferable to change the spatial coordinates of the first and second markers, which are tracked by the optical tracker by moving at least one of the optical tracker, the pattern board, and the camera by at least four times.

In one embodiment, the second step comprises finding, by the processor, the spatial coordinate of the optical center of the camera from the first marker and the spatial coordinate of the origin of the pattern board from the second marker by using the spatial coordinates of the first and second markers from the spatial coordinate of the optical tracker and the spatial coordinate of the origin of the pattern board from the spatial coordinate of the optical center of the camera, which are stored in the processor, adjusting, by the processor, the spatial coordinate of the optical center of the camera by using the spatial coordinate of the optical center of the camera from the first marker and the spatial coordinate of the origin of the pattern board from the second marker which are calculated by the processor, and storing the adjusted spatial coordinate of the optical center of the camera in the processor which is calculated by the processor.

In one embodiment, the spatial coordinate of the optical center of the camera is adjusted by calculating the spatial coordinate of the optical center of the camera from the first marker in a condition that a spatial coordinate of the optical center of the camera from the optical tracker via the first marker is identical to a spatial coordinate of the optical center of the camera via the second marker and the spatial coordinate of the origin of the pattern board.

Meanwhile, the spatial coordinates of the first and second markers of the first step, which are tracked by the optical tracker, may be changed by moving at least once a position of at least one of the optical camera, the pattern board, and the camera.

Advantageous Effects

Thus, a method of registering a camera of a surgical navigation system for an augmented reality comprises attaching a first marker on a camera, attaching a second marker on a pattern board, changing at least once or at least four times spatial coordinates of the first and second markers tracked by an optical tracker, calculating a coordinate of an optical center of the camera, and adjusting a spatial coordinate of the optical center of the camera from the spatial coordinate of the second marker.

As described above, a method of registering a camera of a surgical navigation system for an augmented reality according to an embodiment of the present invention enables single person to do the work by calculating and adjusting the coordinate of the optical center of the camera by moving the optical tracker, the camera, or the pattern board with a second marker attached on the pattern board, not manually attached on the pattern board. And, there is an effect of improving accuracy and safety of a surgery by realizing an augmented reality without generating an accumulated error by the second marker, since the spatial coordinate of the second marker attached on the pattern board maintains uniform.

MODE FOR INVENTION

Figure 1:
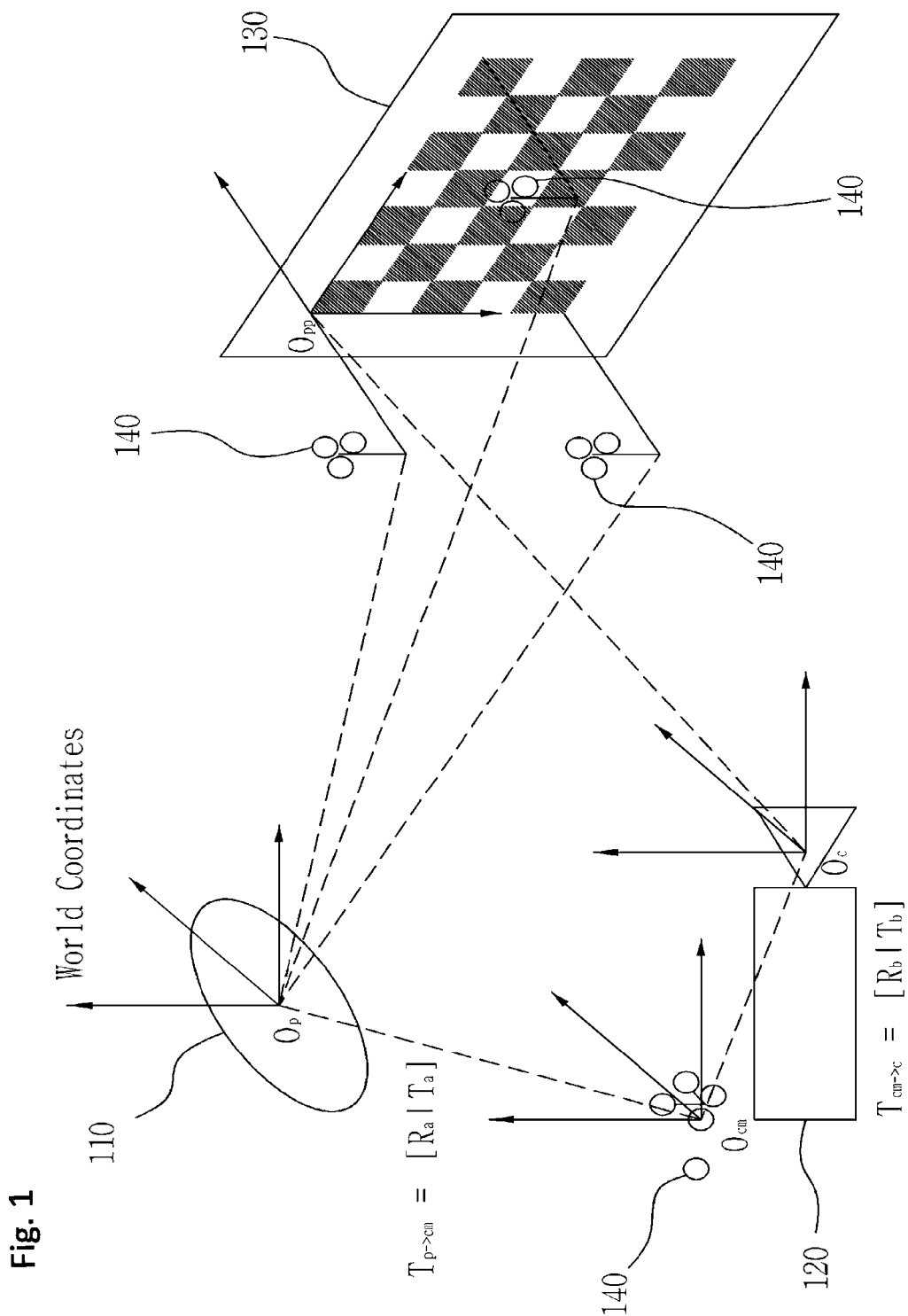
FIG. 1 is a diagram explaining the conventional method of adjusting coordinate of an optical center of a camera.

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that, although the terms first, second, third etc. may be used herein to describe various elements, components, regions, layers and/or sections, these elements, components, and/or sections should not be limited by these terms. These terms are only used to distinguish one element, component, region, layer or section from another region, layer or section. Thus, a first element, component, or section discussed below could be termed a second element, component, or section without departing from the teachings of the present invention.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, with reference to the drawings, preferred embodiments of the present invention will be described in detail.

First Embodiment

Figure 2:
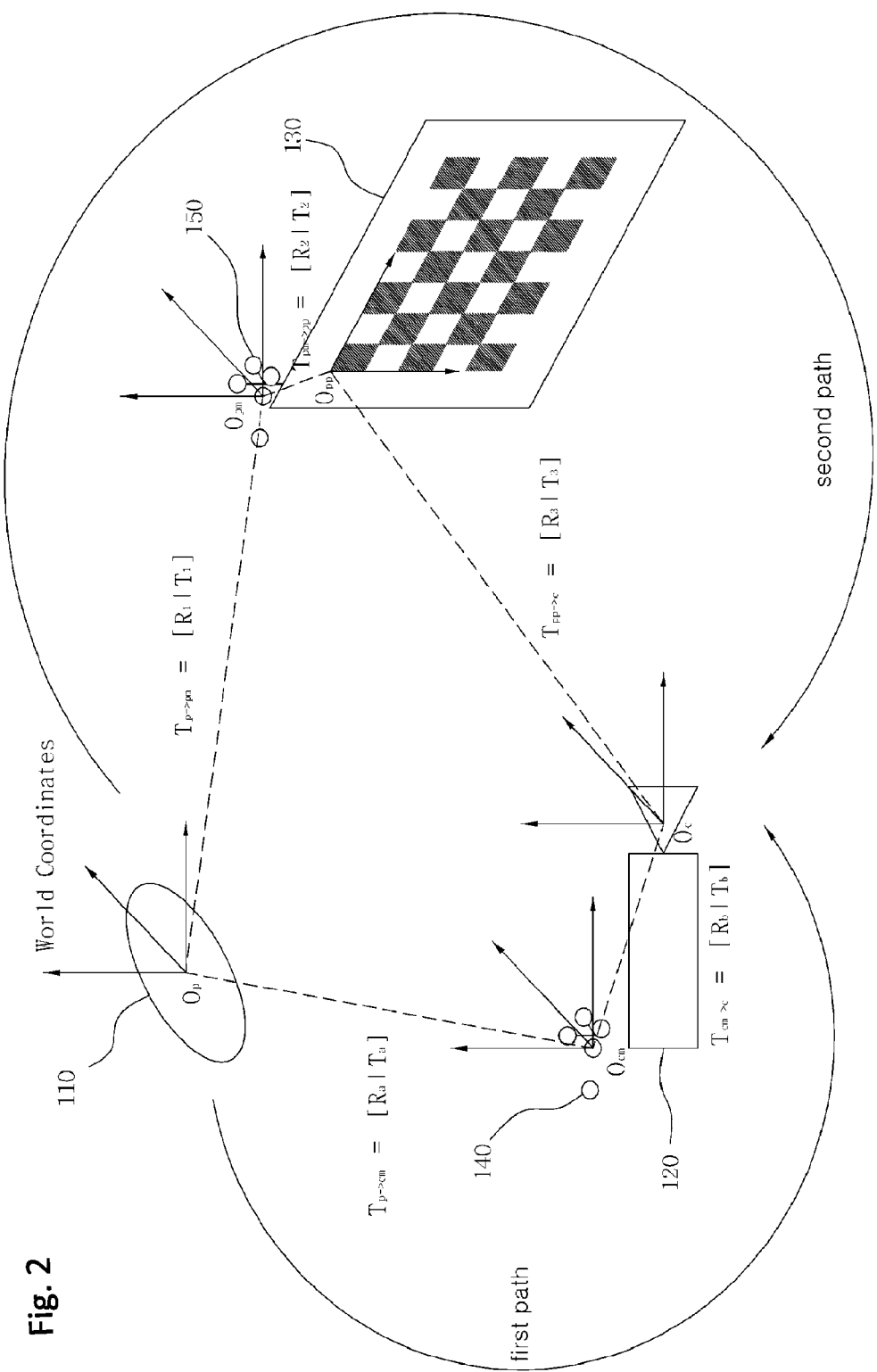
FIG. 2 is a conceptual diagram explaining a method of registering a camera of surgical navigation system for an augmented reality according to a first embodiment of the present invention.
Figure 3:
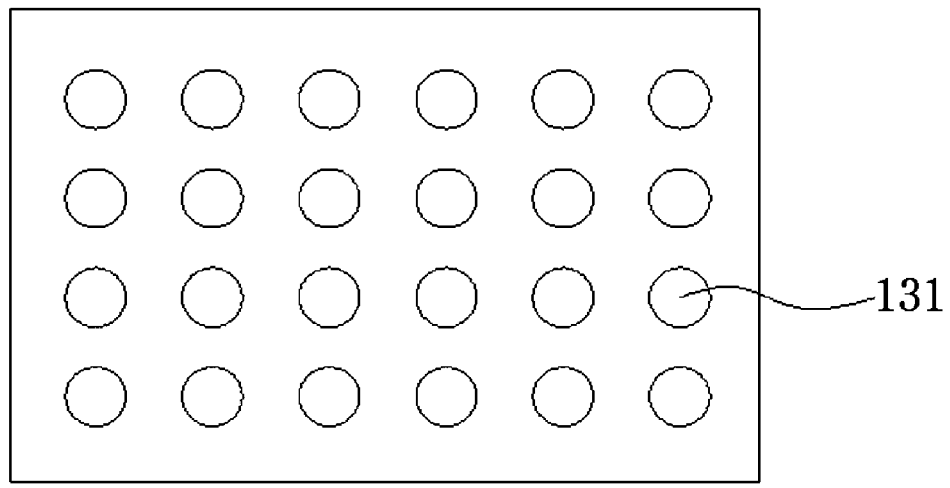
FIG. 3 is another example diagram of a pattern board.
Figure 4:
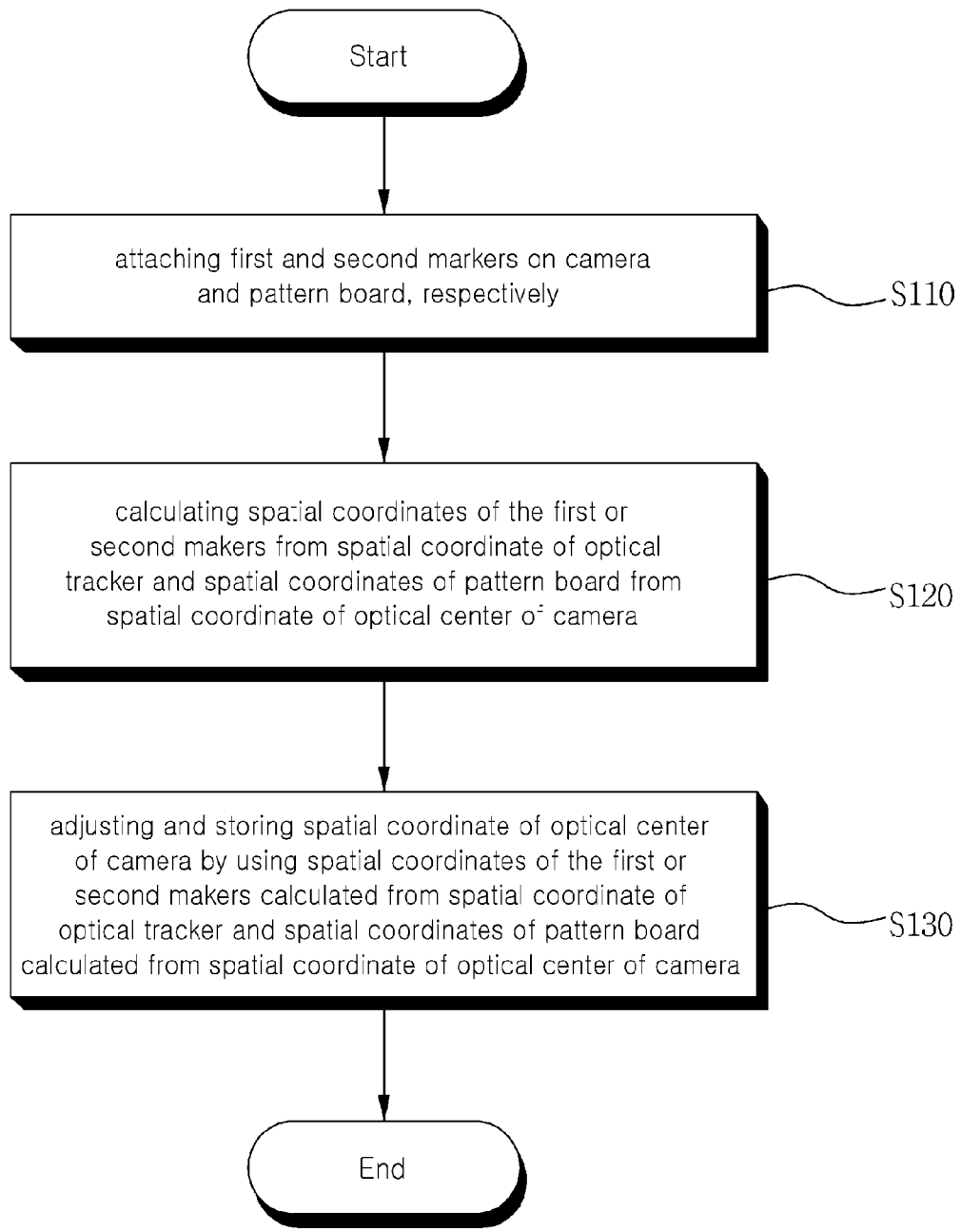
FIG. 4 is a flow chart explaining a method of registering a camera of surgical navigation system for an augmented reality according to a first embodiment of the present invention.

FIG. 2 is a conceptual diagram explaining a method of registering a camera of surgical navigation system for an augmented reality according to a first embodiment of the present invention, FIG. 3 is another example diagram of a pattern board, and FIG. 4 is a flow chart explaining a method of registering a camera of surgical navigation system for an augmented reality according to a first embodiment of the present invention.

Referring to FIGS. 2-4, a method of registering a camera of surgical navigation system for an augmented reality according to a first embodiment of the present invention comprises changing multiple times spatial coordinates of a first marker 140 or a second marker 150 from a spatial coordinate of an optical tracker 110 which tracks the first and second markers 140 and 150 attached on a camera 120 and a pattern board 130, respectively, calculating a spatial coordinate of an optical center of the camera 120, and adjusting the spatial coordinate of the optical center of the camera 120 from the spatial coordinate of the first marker 140. Therefore, it is possible to realize an augmented reality with lowered error compared with the conventional method of registering a camera 120 for augmented reality.

Thus, in order to adjust a spatial coordinate of an optical center of the camera 120 from a spatial coordinate of the first marker 140 according to a method of registering a camera of surgical navigation system for an augmented reality, first, at least one first marker 140 tracked by the optical tracker 110 is attached on the camera, and at least one second marker 150 tracked by the optical tracker 110 is attached on the pattern board 130 (S110).

Herein, a chess board pattern may be formed on the pattern board 130. Meanwhile, the second marker 150 may be attached on the pattern board 130 on which a chess board pattern is formed. Alternatively, the second marker 150 may be attached on the patter board 130 on which a chess board pattern is not formed. In other words, the second marker 150 may be attached on the patter board 130 regardless a position of the pattern board 130 if a light generated from the second marker 150 is tracked by the optical tracker 110. Meanwhile, a circular board pattern 131, except for the chess board pattern, may be formed on the pattern board 130 as shown in FIG. 3. For example, a triangular board pattern, a tetragonal board pattern, and so on may be formed on the pattern board 130.

After attaching the first and second markers 140 and 150 on the camera 120 and the pattern board 130, respectively, spatial coordinates of the first or second makers 140 and 150 tracked by the optical tracker 110 are changed at least two time, and the spatial coordinates of the first and second makers 140 and 150 are found every time from a spatial coordinate of the optical tracker 110 by the processor, at the same time, a spatial coordinate of an origin of the pattern board 130 is calculated from a spatial coordinate of an optical center of the camera 120 (S120).

For example, the spatial coordinates of the first and second markers 140 and 150 tracked by the optical tracker 110 may be changed by moving at least one of the optical tracker 110, the pattern board 130, and the camera 120. And, it may be preferable to move position of the optical tracker 110 or the camera 120.

Meanwhile, it may be preferable to change at least four times the spatial coordinates of the first and second markers 140 and 150 tracked by the optical tracker 10. The reason why the spatial coordinates of the first and second markers 140 and 150 may be changed at least four times will be described on a detailed explanation of the step S120.

After finding and storing in the processor the spatial coordinate of the origin of the pattern board 130 from the spatial coordinate of the optical center of the camera and calculating and storing in the processor the spatial coordinates of the first and second markers 140 and 150 from the spatial coordinate of the optical tracker 110, the spatial coordinate of the optical center of the camera 120 is adjusted and stored in the processor by using the spatial coordinate of the origin of the pattern board 130 from the spatial coordinate of the optical center of the camera and the spatial coordinates of the first and second markers 140 and 150 from the spatial coordinate of the optical tracker 110, which are stored in the processor (S130).

The detailed explanation of the step S120 is described below referring to FIGS. 2, 6, and 6.

Figure 5:
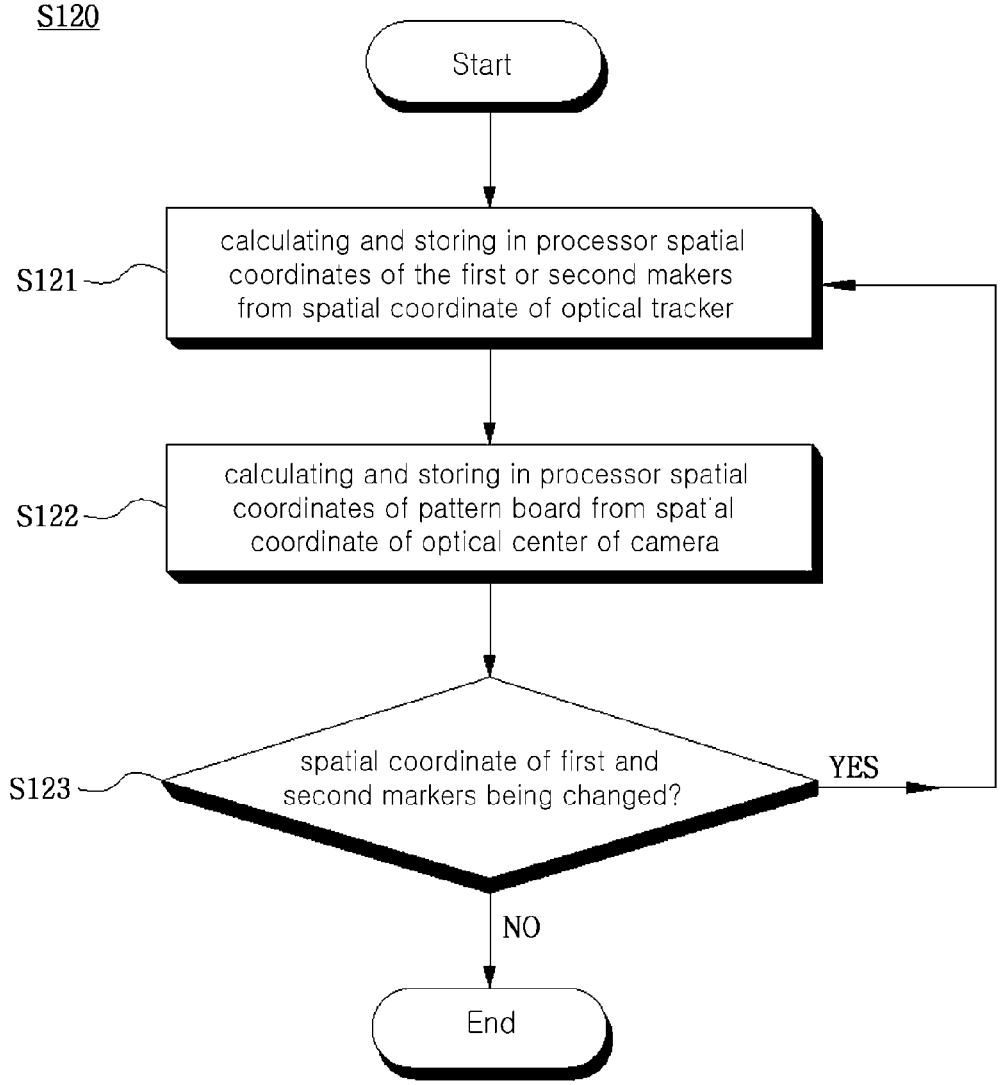
FIG. 5 is a flow chart explaining a step S120.

FIG. 5 is a flow chart explaining a step S120.

Figure 6:
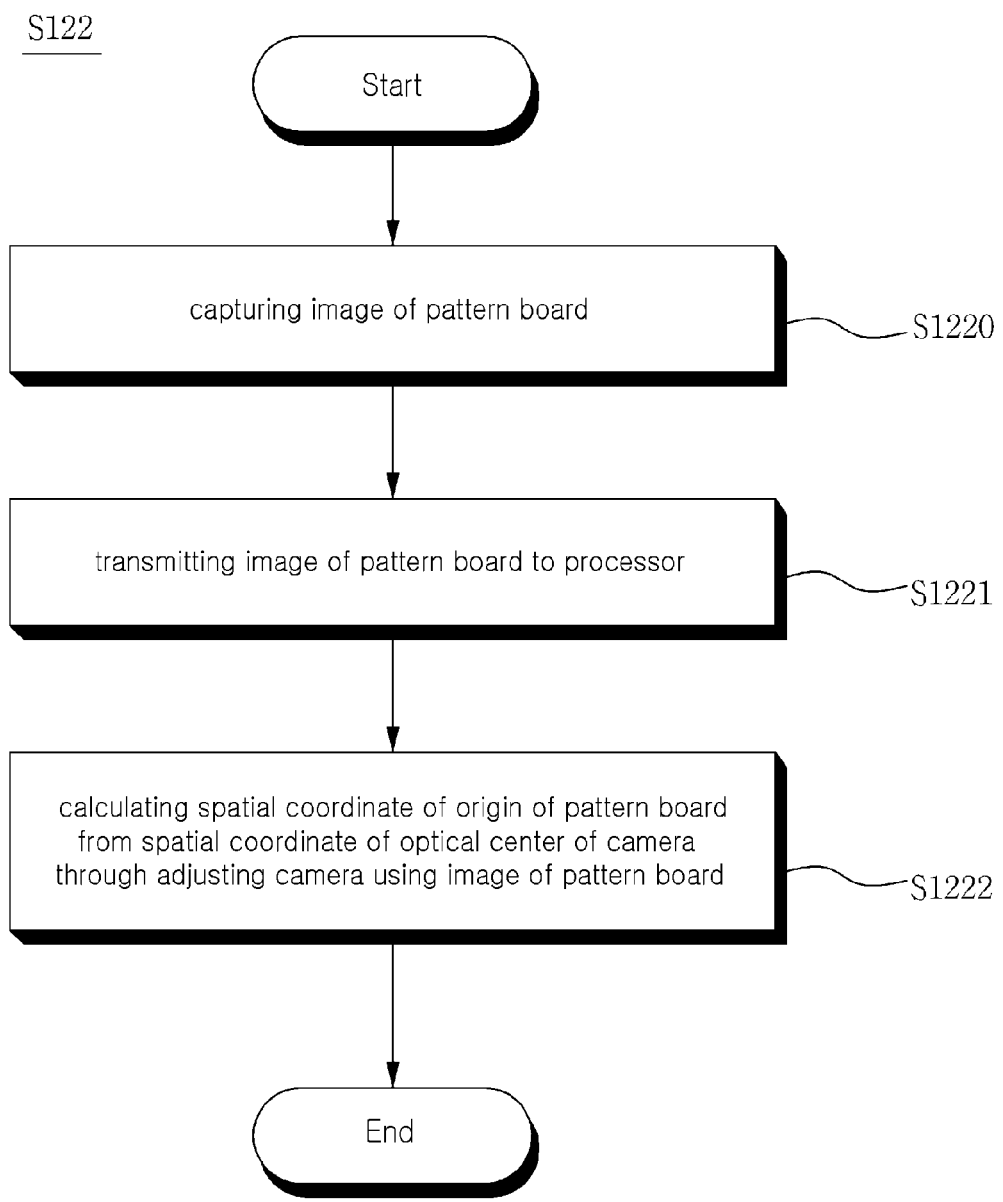
FIG. 6 is a flow chart explaining a step S122.

Referring to FIGS. 2, 5, and 6, during the step S120, first, the first and second markers 140 and 150 are tracked by the optical tracker 110, first spatial coordinates of the first and second markers 140 and 150 are found and stored in the processor, by the processor, from the spatial coordinate of the optical tracker 110 (S121).

Then, first spatial coordinate of the origin of the pattern board 130 is calculated and stored in the processor, by the processor, from the spatial coordinate of the optical center of the camera 120 by using an image of the pattern board 130 obtained from the camera 120 (S122).

Then, the spatial coordinates of the first and second markers 140 and 150 are changed from the spatial coordinate of the optical tracker 110 at least four times, at the same time, by performing the step S122, at least 4 spatial coordinates of the first and second markers 140 and 150 are found and sequentially stored in the processor from the spatial coordinate of the optical tracker 110 and at least 4 spatial coordinates of the origin of the pattern board 130 are calculated and sequentially stored in the processor from the spatial coordinate of the optical center of the camera 120 (S123).

In other words, the steps S121 and S122 are performed each time the spatial coordinate of the first and second markers 140 and 150 are changed from the spatial coordinate of the optical tracker 110, therefore, the spatial coordinates of the first and second markers 140 and 150 from the spatial coordinate of the optical tracker 110 and the spatial coordinate of the pattern board 130 from the spatial coordinate of the optical center of the camera 120 are calculated and stored sequentially in the processor. Therefore, the first spatial coordinates of the first and second markers from the spatial coordinate of the optical tracker 110 from the step S121, and the first spatial coordinate of the origin of the pattern board 130 from the spatial coordinate of the optical center of the camera 120 from the step S122, and at least four spatial coordinates of the first and second markers 140 and 150 calculated from the spatial coordinate of the optical tracker 110 and at least four spatial coordinates of the origin of the pattern board 130 from the spatial coordinate of the optical center of the camera 120 from the step S123 are stored in the processor.

Therefore, at least five spatial coordinates of the first and second markers 140 and 150 from the spatial coordinate of the optical tracker 110, and at least five spatial coordinates of the origin of the pattern board 130 from the spatial coordinate of the optical center of the camera 120 are stored in the processor.

Referring ti FIG. 6, during the step S122, first, an image of the pattern board 130 is obtained by the camera 120 (S1220).

Then, the image of the pattern board 130 obtained by the camera 120 is transmitted to the processor (S1221).

After transmitting the image of the pattern board 130 obtained by the camera 120, the spatial coordinate of the origin of the pattern board 130 is calculated by the processor from the spatial coordinate of the optical center of the camera 120 through adjusting the camera 120 using the obtained image (S1222). Herein, the spatial coordinate of the origin of the pattern board 130 calculated from the spatial coordinate of the optical center of the camera 120, which is calculated through adjusting the camera 120 using the obtained image, may be calculated by using a general method of Zhang.

The detailed explanation of the step S130 is described below referring to FIGS. 2, and 7.

Figure 7:
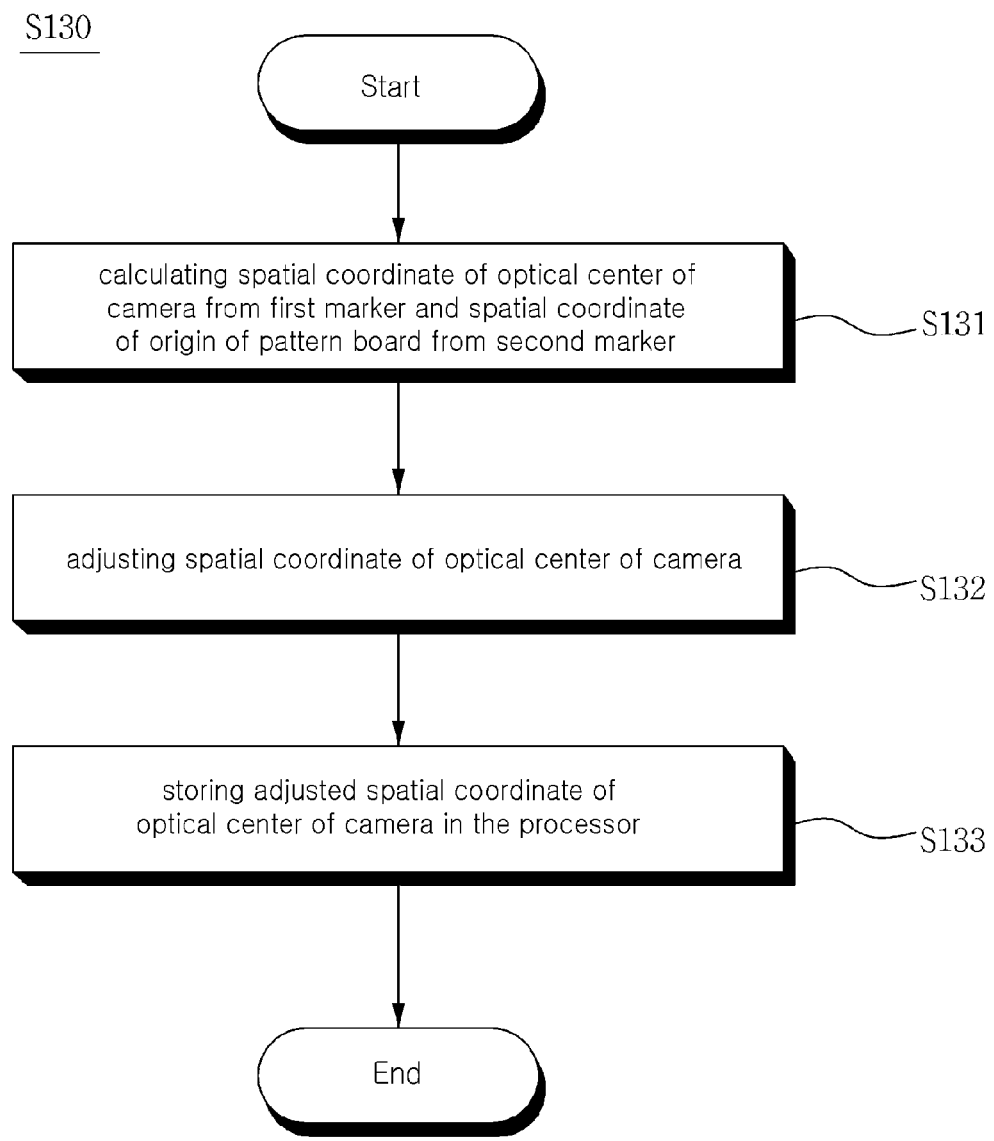
FIG. 7 is a flow chart explaining a step S130.

FIG. 7 is a flow chart explaining a step S130.

Referring to FIGS. 2 and 7, during the step S130, the spatial coordinate of the optical center of the camera 120 is calculated from the first marker 140 and the spatial coordinate of the origin of the pattern board 130 is calculated from the second marker 150, by the processor, by using the spatial coordinates of the first and second markers 140 and 150 from the spatial coordinate of the optical tracker, which are found before by the processor, and the spatial coordinates of the origin of the pattern boards 130 from the spatial coordinate of the optical center of the camera 120.

In other words, spatial coordinate of the optical center of the camera is calculated from the first marker 140 and spatial coordinate of the origin of the pattern board 130 is calculated from the second marker 150 by the processor by using the spatial coordinates of the first and second markers 140 and 150 from the first spatial coordinate of the optical tracker 110 which is stored in the processor from the step S121, the first spatial coordinate of the origin of the pattern board 130 from the spatial coordinate of the optical center of the camera 120 which is stored in the processor from the step S122, at least four spatial coordinates of the first and second markers 140 and 150 from the spatial coordinate of the optical tracker 110 which are stored in the processor from the step S123, and at least four spatial coordinates of the origin of the pattern board 130 from the spatial coordinate of the optical center of the camera 120 which are stored in the processor from the step S123.

In other words, during the step S131, the spatial coordinate of the optical center of the camera is calculated from the first marker 140 and the spatial coordinate of the origin of the pattern board 130 is calculated from the second marker 150 by the processor by using at least five spatial coordinates of the first and second markers 140 and 150 from the optical tracker 110 and at least five spatial coordinates of the origin of the pattern board 130 from the spatial coordinate of the optical center of the camera 120 which are stored in the processor.

Then, the spatial coordinate of the optical center of the camera 120 is adjusted by the processor by using the spatial coordinate of the optical center of the camera from the first marker 140 and the spatial coordinate of the origin of the pattern board 130 from the second marker 150 (S132).

Then, the adjusted spatial coordinate of the optical center of the camera 120 is stored in the processor (S133).

Meanwhile, during the step S132, spatial coordinate of the optical center of the camera 120 is adjusted by calculating the spatial coordinate of the optical center of the camera 120 from the first marker 140 in a condition that a spatial coordinate of the optical center of the camera 120 from the optical tracker 110 via the first marker 140 (first path) is identical to a spatial coordinate of the optical center of the camera 120 from the optical tracker 110 via the second marker 150 and the origin of the pattern board 130 (second path).

In other words, in the step S132, the spatial coordinate of the optical center of the camera 120 is adjusted by the processor by calculating the spatial coordinate of the optical center of the camera 120 from the first marker 140 in a condition that a spatial coordinate of the optical center of the camera via the first path is identical to a spatial coordinate of the optical center of the camera via the second path are identical as shown in FIG. 2.

The reason why at least five spatial coordinates of the first and second markers 140 and 140 found from the spatial coordinate of the optical tracker 110 and at least five spatial coordinates of the origin of the pattern board 130 from the spatial coordinate of the optical center of the camera 120 are used to calculate the spatial coordinate of the origin of the pattern board 130 is described with reference to FIG. 2. In other words, the reason why the spatial coordinates of the first and second markers 140 and 150 may be changed at least four times of the step S120 is described in below.

Referring to FIG. 2, an origin of the optical tracker which uses a world spatial coordinate is defined as $O_p$, an origin of the first marker 140 attached on the camera 120 is defined as $O_{cm}$, an origin of the second marker 150 attached on the pattern board is defined as $O_{pm}$, an origin of the pattern board 130 is defined as $O_{pp}$, and the spatial coordinate of the first marker 140 ($T_{p \to cm}$) attached on the camera 120 and moved in parallel from the optical tracker 110 may be expressed by an Equation 1.

$$T_{p \to cm} = [R_a | T_a] \qquad \text{[Equation 1]}$$

Herein, R means a correlation of an orientation of a spatial coordinate, T means a correlation of a distance of a spatial coordinate. In other words, $R_a$ of the Equation 1 means a correlation of an orientation between a spatial coordinate of an optical tracker 110 and a spatial coordinate of a first marker 140, and $T_a$ means a correlation of a distance between a spatial coordinate of an optical tracker 110 and a spatial coordinate of a first marker 140. Hereafter, explanation of an Equation is omitted.

Also, a spatial coordinate of the optical center of the camera 120 ($T_{cm \to c}$) which is moved in parallel from a spatial coordinate of the first marker 140 may be expressed by an Equation 2.

$$T_{cm \to c} = [R_b | T_b] \quad \text{[Equation 2]}$$

Therefore, a spatial coordinate of the optical center of the camera 120 which is moved in parallel from a spatial coordinate of the optical tracker 110 via an origin of the first marker 140, in other words, a spatial coordinate of the optical center of the camera 120 which is moved in parallel from the spatial coordinate of the optical tracker 110 via a first path ($T_{p \to cm} T_{cm \to c}$) may be expressed by an Equation 3 ("O" represents a zero matrix, and "I" indicates a unit matrix).

[Equation 3]
$$T_{p \to cm} T_{cm \to c} = \begin{bmatrix} R_a | T_a \\ O | I \end{bmatrix} \begin{bmatrix} R_b | T_b \\ O | I \end{bmatrix} = \begin{bmatrix} R_a R_b & | & R_a T_b + T_a \\ O & | & I \end{bmatrix}$$

Meanwhile, a spatial coordinate of the second marker 150 attached on the patter board 130 and moved in parallel from the spatial coordinate of the optical tracker 110 may be expressed by an Equation 4.

$$T_{p \to pm} = [R_1 | T_1] \quad \text{[Equation 4]}$$

Also, a spatial coordinate of the origin of the pattern board ($T_{pm \to pp}$) which is moved in parallel from the spatial coordinate of the second marker 150 may be expressed by an Equation 5.

$$T_{pm \to pp} = [R_2 | T_2] \quad \text{[Equation 5]}$$

Also, a spatial coordinate of the optical center of the camera 120 ($T_{pp \to c}$) which is moved in parallel from the spatial coordinate of the pattern board 130 may be expressed by an Equation 6.

$$T_{pp \to c} = [R_3 | T_3] \quad \text{[Equation 6]}$$

Therefore, a spatial coordinate of the optical center of the camera 120 which is moved in parallel from the spatial coordinate of the optical tracker 110 via the origin of the second marker 150 and the origin of the pattern board 130, in other words, a spatial coordinate of the optical center of the camera 120 ($T_{pp \to c} T_{pm \to pp} T_{p \to pm}$) from the spatial coordinate of the optical tracker 110 via the second path may be expressed by an Equation 7.

[Equation 7]
$$T_{p \to pm} T_{pm \to pp} T_{pp \to c} = \begin{bmatrix} R_1 | T_1 \\ O | I \end{bmatrix} \begin{bmatrix} R_2 | T_2 \\ O | I \end{bmatrix} \begin{bmatrix} R_3 | T_3 \\ O | I \end{bmatrix}$$
$$= \begin{bmatrix} R_1 R_2 R_3 & | & R_1 R_2 T_3 + R_1 T_2 + T_1 \\ O & | & I \end{bmatrix}$$

And, a result such as Equations 8 and 9 comes out since spatial coordinates of the optical center of the camera via the first and second paths are identical.

$$R_a R_b = R_1 R_2 R_3 \quad \text{[Equation 8]}$$

$$R_a T_b + T_a = R_1 R_2 T_3 + R_1 T_2 + T_1 \quad \text{[Equation 9]}$$

Therefore, $R_1 R_2$ may be substituted as Equation 10 by the Equation 8.

$$R_1 R_2 = R_a R_b R_3^{-1} \quad \text{[Equation 10]}$$

Therefore, Equation 11 is expressed by substituting $R_a R_b R_3^{-1}$ for $R_1 R_2$ in the Equation 9.

$$R_a T_b + T_a = R_a R_b R_3^{-1} T_3 + R_1 T_2 + T_1 \quad \text{[Equation 11]}$$

Equation 12 may be expressed by organizing the Equation 11.

$$R_b R_3^{-1} T_3 - T_b + T_a^{-1} R_1 T_2 = R_a^{-1} (T_a - T_1) \quad \text{[Equation 12]}$$

And, $T_A$ is substituted for $R_3^{-1} T_3$ in the Equation 12, $R_A$ is substituted for $R_a^{-1} R_1$, and $T_K$ is substituted for $R_a^{-1}(T_a - T_1)$. Meanwhile, each of the $R_b$, $T_A$, $T_b$, $R_A$, $T_2$, and $T_K$ may be expressed by Equations 13 to 18.

[Equation 13]
$$R_a = \begin{bmatrix} r_{11\_b} & r_{12\_b} & r_{13\_b} \\ r_{21\_b} & r_{12\_b} & r_{23\_b} \\ r_{31\_b} & r_{32\_b} & r_{33\_b} \end{bmatrix}$$

[Equation 14]
$$T_A = \begin{bmatrix} T_{1\_A} \\ T_{2\_A} \\ T_{3\_A} \end{bmatrix}$$

[Equation 15]
$$T_b = \begin{bmatrix} T_{1\_b} \\ T_{2\_b} \\ T_{3\_b} \end{bmatrix}$$

[Equation 16]
$$R_a = \begin{bmatrix} r_{11\_A} & r_{12\_A} & r_{13\_A} \\ r_{21\_A} & r_{12\_A} & r_{23\_A} \\ r_{31\_A} & r_{32\_A} & r_{33\_A} \end{bmatrix}$$

[Equation 17]
$$T_2 = \begin{bmatrix} T_{1\_2} \\ T_{2\_2} \\ T_{3\_2} \end{bmatrix}$$

[Equation 18]
$$T_K = \begin{bmatrix} T_{1\_K} \\ T_{2\_K} \\ T_{3\_K} \end{bmatrix}$$

Therefore, the Equation 12 may be expressed by the Equation 19 by substituting $R_b$, $T_A$, $T_b$, $R_a$, $T_2$, and $T_K$, which are expressed by Equations 13 to 18.

[Equation 19]

$$\begin{bmatrix} T_{1\_A} & T_{2\_A} & T_{3\_A} & 0 & 0 & 0 & 0 & 0 & 0 & -1 & 0 & 0 & r_{11\_A} & r_{12\_A} & r_{13\_A} \\ 0 & 0 & 0 & T_{1\_A} & T_{2\_A} & T_{3\_A} & 0 & 0 & 0 & 0 & -1 & 0 & r_{21\_A} & r_{12\_A} & r_{23\_A} \\ 0 & 0 & 0 & 0 & 0 & 0 & T_{1\_A} & T_{2\_A} & T_{3\_A} & 0 & 0 & -1 & r_{31\_A} & r_{32\_A} & r_{33\_A} \end{bmatrix} \begin{bmatrix} r_{11\_b} \\ r_{12\_b} \\ r_{13\_b} \\ r_{21\_b} \\ r_{22\_b} \\ r_{23\_b} \\ r_{31\_b} \\ r_{32\_b} \\ r_{33\_b} \\ T_{1\_b} \\ T_{2\_b} \\ T_{3\_b} \\ T_{1\_2} \\ T_{2\_2} \\ T_{3\_2} \end{bmatrix} = \begin{bmatrix} T_{1\_K} \\ T_{2\_K} \\ T_{3\_K} \end{bmatrix}$$

The unknown parameters, r11_b, r12_b, r13_b, r21_b, r22_b, r23_b, r31_b, r32_b, r33_b, T1_b, T2_b, T3_b, T1_2, T2_2, T3_2, to be calculated are fifteen, and therefore, at least one of the optical tracker 110, the camera 120, and the pattern board 130 may be moved at least four times or at least one of the camera 120 and the pattern board 130 may be moved at least four times to solve the Equations since three Equations are generated from one configuration.

Therefore, spatial coordinates of the first and second markers 140 and 150 are changed at least four times, at least five spatial coordinates of the first and second markers 140 and 150 from the spatial coordinate of the optical tracker 110 and at least five spatial coordinates of the origin of the pattern board 1230 from the spatial coordinate of the optical center of the camera 120 are stored in the processor, and the spatial coordinate of the optical center of the camera 120 is adjusted by the processor by calculating the spatial coordinate of the optical center of the camera 120 from the first marker 140 and the spatial coordinate of the origin of the pattern board 120 from the second marker 150.

As described above, a method of registering a camera of surgical navigation system for an augmented reality comprises attaching a second marker 150 on a pattern board 130, changing at least four times spatial coordinates of the first and second markers 140 and 150, and adjusting the spatial coordinate of the optical center of the camera 120 from a spatial coordinate of a second marker 150.

As described above, a method of registering a camera of a surgical navigation system for an augmented reality according to an embodiment of the present invention enables single person to do the work by calculating and adjusting coordinate of an optical center of a camera 120 by moving an optical tracker 110, the camera 120, or a pattern board 130 with a second marker 150 attached on the pattern board 130, not manually attached on the pattern board 130. And, there is an effect of improving accuracy and safety of a surgery by realizing an augmented reality without generating an accumulated error by the second marker, since the spatial coordinate of the second marker attached on the pattern board maintains uniform.

Second Embodiment

Figure 8:
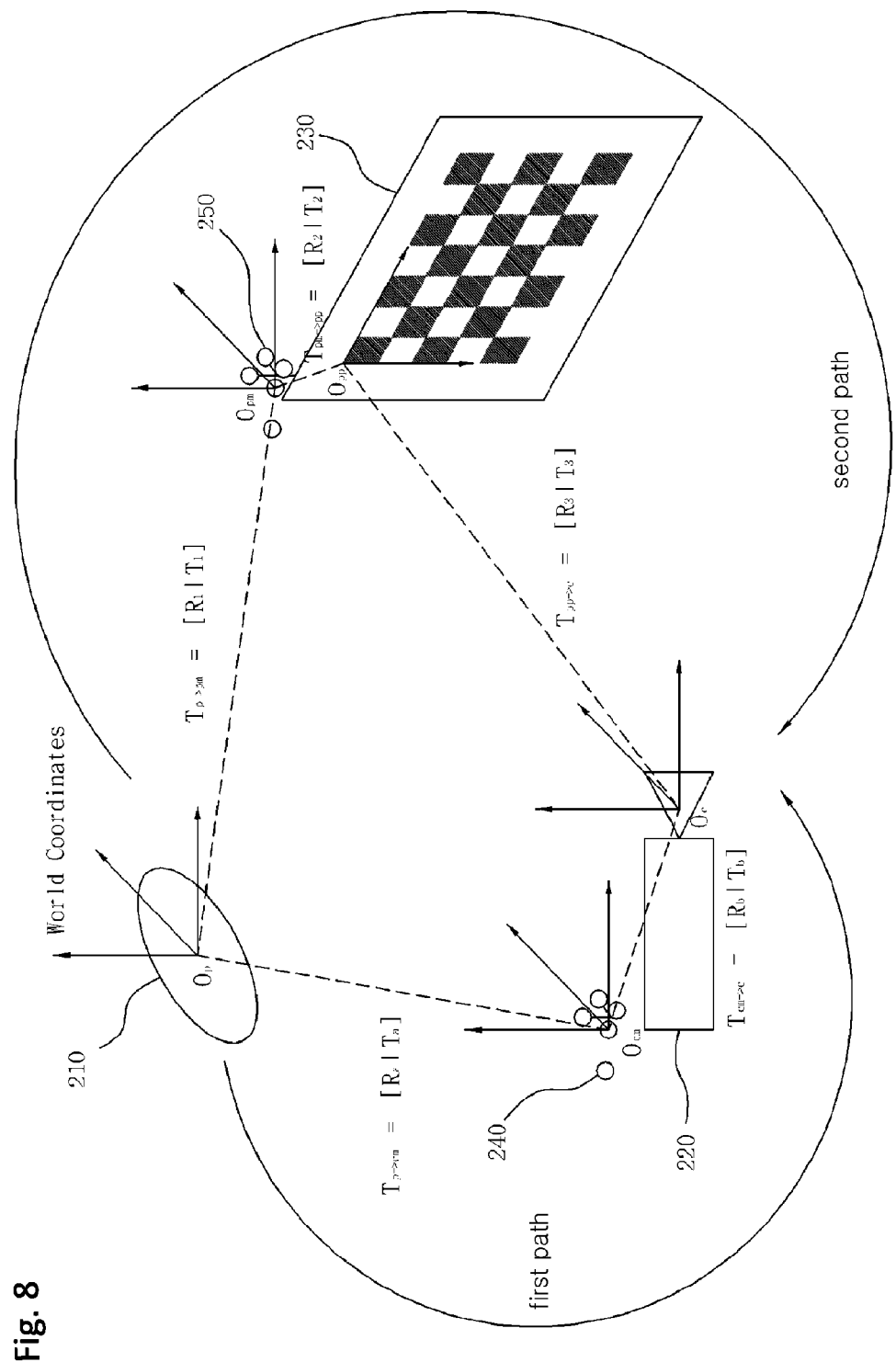
FIG. 8 is a conceptual diagram explaining a method of registering a camera of surgical navigation system for an augmented reality according to a second embodiment of the present invention.
Figure 9:
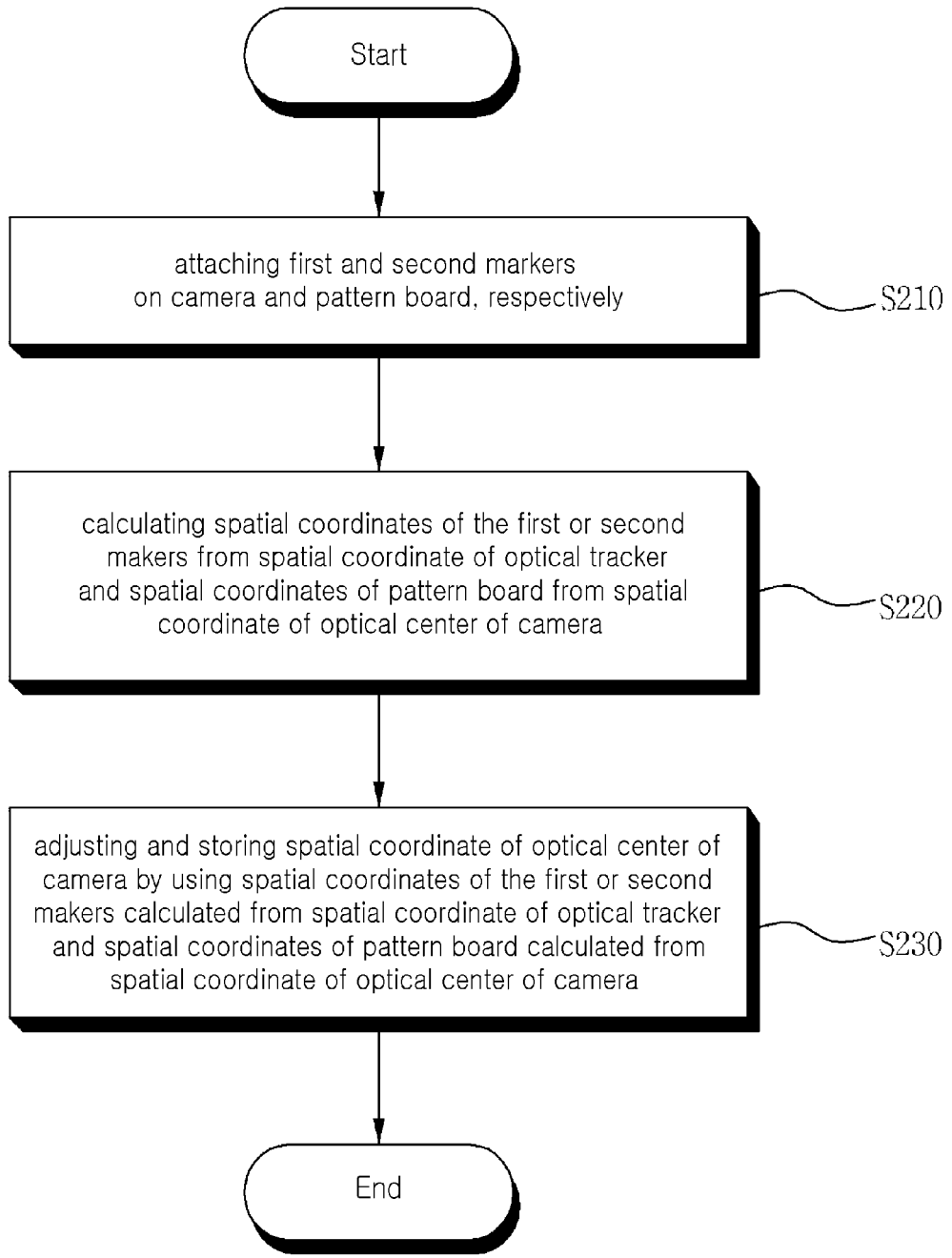
FIG. 9 is a flow chart explaining a method of registering a camera of surgical navigation system for an augmented reality according to a second embodiment of the present invention.
Figure 10:
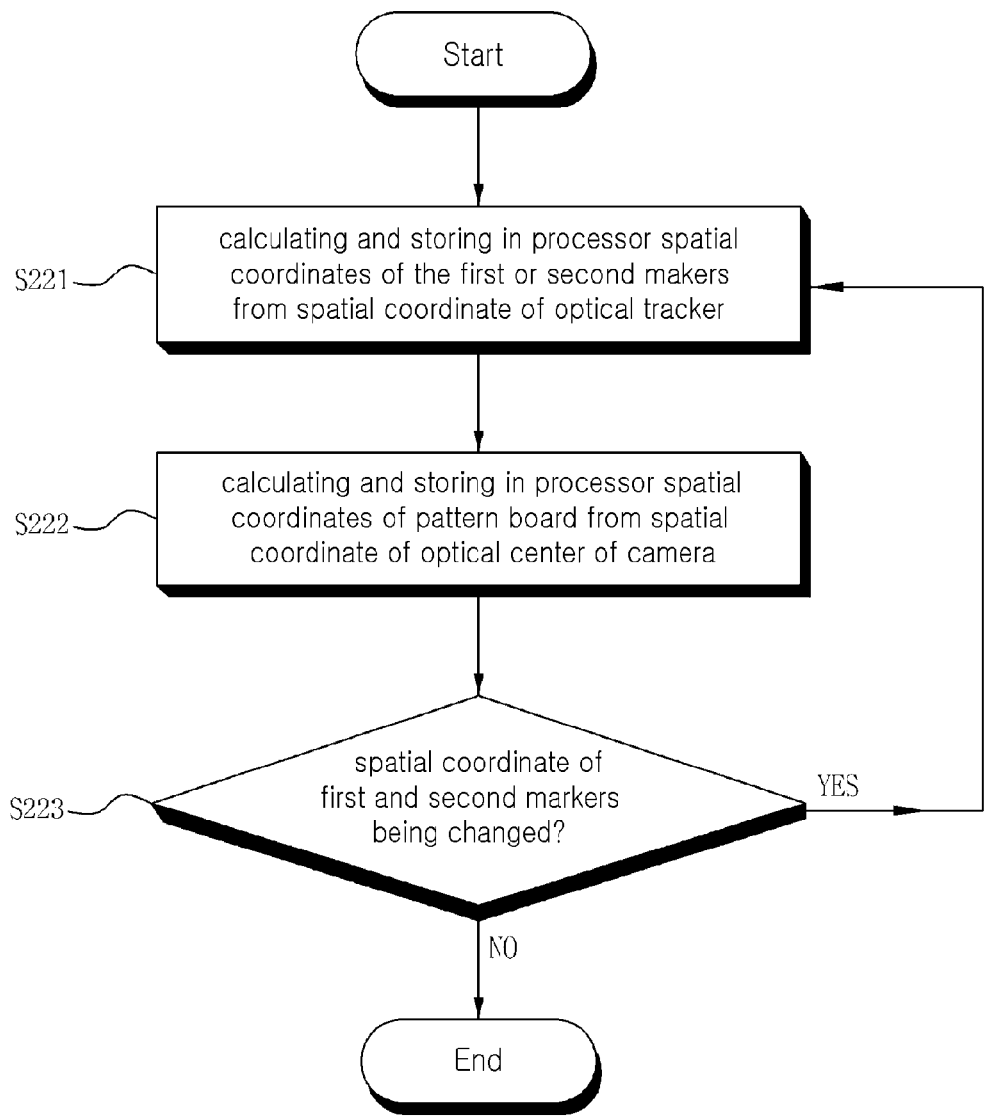
FIG. 10 is a flow chart explaining a step S220.

FIG. 8 is a conceptual diagram explaining a method of registering a camera of surgical navigation system for an augmented reality according to a second embodiment of the present invention, FIG. 9 is a flow chart explaining a method of registering a camera of surgical navigation system for an augmented reality according to a second embodiment of the present invention, and FIG. 10 is a flow chart explaining step S220.

A method of registering a camera of a surgical navigation system for an augmented reality according to an embodiment of the present invention is substantially the same as the method of registering a camera according to the first embodiment except for steps S220 and S230, explanations of other method except for steps S220 and S230 are omitted.

Referring to FIGS. 8 and 10, during the step S220 according to an embodiment, first, first and second markers 240 and 250 are tracked by the optical tracker 220, first spatial coordinates of the first and second markers 240 and 250 are found from a spatial coordinate of the optical tracker 210 by a processor, and the first spatial coordinates of the first and second markers 240 and 250 are stored in the processor (S221).

Then, a spatial coordinate of an origin of the pattern board 230 is first calculated from a spatial coordinate of an optical center of the camera 220 by the processor by using an image of the pattern board 230 obtained from the camera 220, and the first spatial coordinate of an optical center of the camera 220 is stored in the processor (S222).

Then, spatial coordinates of the first and second markers 240 and 250 are changed multiple times, at least once, and at the same time, at least one spatial coordinate of the first and second markers 240 and 250 from the spatial coordinate of the optical tracker 210 are found and at least one spatial coordinate of an origin of the pattern board 230 from the spatial coordinate of the optical center of the camera 220 are calculated by the processor and stored sequentially in the processor by performing the steps S221 and S222 each time the spatial coordinates of the first and second markers 240 and 250 are changed (S223).

In other words, the steps S221 and S222 are performed each time the first and second markers 240 and 250 are changed from the spatial coordinate of the optical tracker 210, spatial coordinates of the first and second markers 240 and 250 are found from the spatial coordinate of the optical tracker 110 and spatial coordinate of the origin of the pattern board 230 from the spatial coordinate of the optical center of the camera 220 are calculated and stored, sequentially, in the processor, and therefore, the first spatial coordinates of the first and second markers 240 and 250 from the spatial coordinate of the optical tracker 210 which are obtained from the step S221, the first spatial coordinate of the origin of the pattern board 230 from the spatial coordinate of the optical center of the camera 220 which is obtained from the step S222, at least one spatial coordinates of the first and second markers 240 and 250 from the spatial coordinate of the optical tracker 210, and at least one spatial coordinate of the origin of the pattern board 230 from the spatial coordinate of the optical center of the camera 220 which are obtained from the step S233 are stored in the processor.

Thus, at least two spatial coordinates of the first and second markers 240 and 250 from the spatial coordinate of the optical tracker 210, and at least two spatial coordinate of the origin of the pattern board 230 from the spatial coordinate of the optical center of the camera 220 are stored in the processor.

Figure 11:
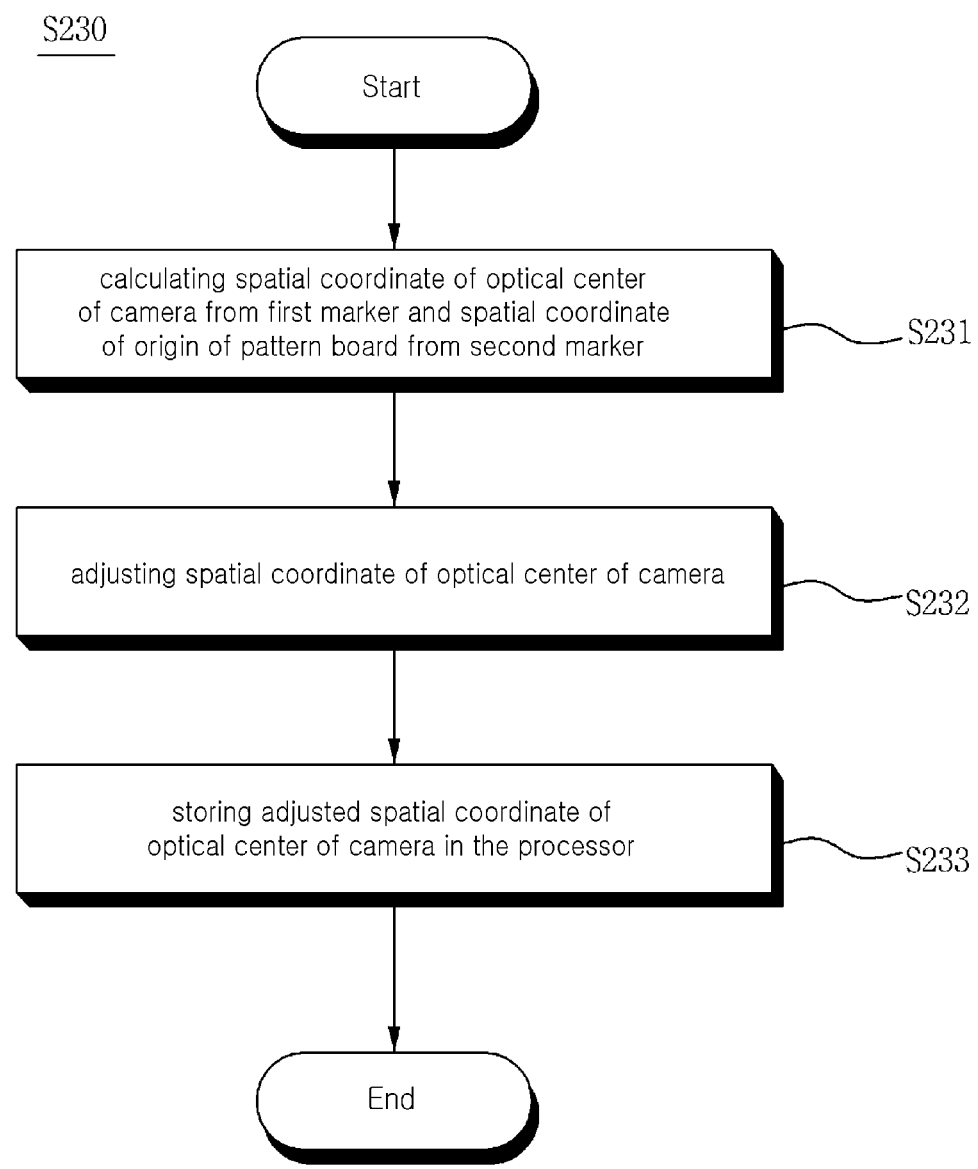
FIG. 11 is a flow chart explaining a step S230.

FIG. 11 is a flow chart explaining step S230.

Referring to FIGS. 8 and 11, during the step 230, first, spatial coordinate of the optical center of the camera and spatial coordinate of the origin of the pattern board 230 are calculated from the first marker 240 and the second marker 250, respectively, by the processor by using the spatial coordinates of the first and second markers 240 and 250 from the spatial coordinate of the optical tracker 210 and the spatial coordinate of the origin of the pattern board 230 from the spatial coordinate of the optical center of the camera 220, which are found and calculated by the processor (S231).

In other words, spatial coordinate of the optical center of the camera and spatial coordinate of the origin of the pattern board 230 are calculated from the first marker 240 and the second marker 250, respectively, by using the spatial coordinate of the first and second markers 140 and 150 from the spatial coordinate of the optical tracker which are stored in the processor from the step S221, the spatial coordinate of the origin of the pattern board 230 from the spatial coordinate of the optical center of the camera 220 which is stored in the processor from the step S222, spatial coordinates of the first and second markers 240 and 250 from at least one spatial coordinate of the optical tracker 210 which are stored in the processor from the step S223, and spatial coordinates of the origin of the pattern board 230 from the at least one spatial coordinate of the optical center of the camera 220 which are stored in the processor from the step S223.

In other words, the spatial coordinate of the optical center of the camera and the spatial coordinate of the origin of the pattern board 230 are calculated from the first marker 240 and the second marker 250, respectively, by using the at least two spatial coordinates of the first and second markers 240 and 250 from the optical tracker 210 and at least two spatial coordinates of the origin of the pattern board 230 from the spatial coordinate of the optical center of the camera 220, which are stored in the processor from the step S231.

Then, the spatial coordinate of the optical center of the camera 220 is adjusted by the processor by using the spatial coordinate of the optical center of the camera 220 calculated from the first marker 240 and the spatial coordinate of the origin of the pattern board 230 calculated from the second marker 250 (S232).

Then, the adjusted spatial coordinate of the optical center of the camera 220 by the processor is stored in the processor (S233).

Meanwhile, during the step S232, the spatial coordinate of the optical center of the camera 220 is calculated and adjusted from the spatial coordinate of the first marker 240 by the processor in a condition that the spatial coordinate of the optical center of the camera 220 from the optical tracker 210 via the first marker 240 (first path) and the spatial coordinate of the optical center of the camera 220 from the optical tracker 210 via the second marker 250 and the pattern board 230 (second path) are identical.

In other words, during the step S232, the spatial coordinate of the optical center of the camera 220 is adjusted by the processor by calculating the spatial coordinate of the optical center of the camera 220 from the first marker 240 in a condition that a spatial coordinate of the optical center of the camera via the first path and a spatial coordinate of the optical center of the camera via the second path are identical as shown in FIG. 8.

The reason why at least two first and second markers 240 and 240 from the spatial coordinate of the optical tracker 210, at least two spatial coordinate of the origin of the pattern board 230 from the spatial coordinate of the optical center of the camera 220 are used to calculate the spatial coordinate of the origin of the pattern board 230 is described with reference to FIG. 8. In other words, the reason why the spatial coordinates of the first and second markers 140 and 150 are changed at least once of the step S120 is described in below.

Referring to FIG. 8, an origin of the optical tracker 210 which uses a world spatial coordinate is defined as $O_p$, an origin of the first marker 240 attached on the camera 220 is defined as $O_{cm}$, an origin of the second marker 250 attached on the pattern board 230 is defined as $O_{pm}$, an origin of the pattern board 230 is defined as $O_{pp}$, and the spatial coordinate of the first marker 140 ($T_{p \to cm}$) attached on the camera 220 and moved in parallel from the optical tracker 210 may be expressed by an Equation 20.

$$T_{p \to cm} = [R_a | T_a] \qquad \text{[Equation 20]}$$

Herein, R means a correlation of an orientation of a spatial coordinate, T means a correlation of a distance of a spatial coordinate. In other words, $R_a$ of the Equation 20 means a correlation of an orientation between a spatial coordinate of the optical tracker 110 and a spatial coordinate of a first marker 240, and $T_a$ means a correlation of a distance between a spatial coordinate of the optical tracker 210 and a spatial coordinate of the first marker 240. Hereafter, explanation of an Equation is omitted.

Also, a spatial coordinate of the optical center of the camera 220 ($T_{cm \to c}$) which is moved in parallel from a spatial coordinate of the first marker 240 may be expressed by an Equation 21.

$$T_{cm \to c} = [R_b | T_b] \qquad \text{[Equation 21]}$$

Therefore, a spatial coordinate of the optical center of the camera 220 which is moved in parallel from a spatial coordinate of the optical tracker 210 via the origin of the first marker 240, in other words, a spatial coordinate of the optical center of the camera 220 which is moved in parallel from a spatial coordinate of the optical tracker 210 via the first path ($T_{p \to cm} T_{cm \to c}$) may be expressed by an Equation 22.

[Equation 22]

$$T_{p \to cm}T_{cm \to c} = \begin{bmatrix} R_a | T_a \\ O | I \end{bmatrix}\begin{bmatrix} R_b | T_b \\ O | I \end{bmatrix} = \begin{bmatrix} R_a R_b & | & R_a T_b + T_a \\ O & | & I \end{bmatrix}$$

Meanwhile, a spatial coordinate of the second marker 250 attached on the patter board 230 and moved in parallel from a spatial coordinate of the optical tracker 210 may be expressed by an Equation 23.

$$T_{p \to pm} = [R_1 | T_1] \quad \text{[Equation 23]}$$

Also, a spatial coordinate of the origin of the pattern board ($T_{pm \to pp}$) which is moved in parallel from a spatial coordinate of the second marker 250 may be expressed by an Equation 24.

$$T_{pm \to pp} = [R_2 | T_2] \quad \text{[Equation 24]}$$

Also, a spatial coordinate of the optical center of the camera 120 ($T_{pp \to c}$) which is moved in parallel from a spatial coordinate of the pattern board 130 may be expressed by an Equation 25.

$$T_{pp \to c} = [R_3 | T_3] \quad \text{[Equation 25]}$$

Therefore, a spatial coordinate of the optical center of the camera 120 which is moved in parallel from a spatial coordinate of the optical tracker 110 via the origin of the second marker 150 and the origin of the pattern board 130, in other words, a spatial coordinate of the optical center of the camera 120 ($T_{pp \to c} T_{pm \to pp} T_{p \to pm}$) from a spatial coordinate of the optical tracker 110 via the second path may be expressed by an Equation 26.

[Equation 26]

$$T_{p \to pm}T_{pm \to pp}T_{pp \to c} = \begin{bmatrix} R_1 | T_1 \\ O | I \end{bmatrix}\begin{bmatrix} R_2 | T_2 \\ O | I \end{bmatrix}\begin{bmatrix} R_3 | T_3 \\ O | I \end{bmatrix}$$

$$= \begin{bmatrix} R_1 R_2 R_3 & | & R_1 R_2 T_3 + R_1 T_2 + T_1 \\ O & | & I \end{bmatrix}$$

And, a result, such as Equations 27 and 28, comes out by comparing the Equations 22 and 26 since spatial coordinates of the optical center of the camera 220 via the first and second paths are identical.

$$R_a R_b = R_1 R_2 R_3 \quad \text{[Equation 27]}$$

$$R_a T_b + T_a = R_1 R_2 T_3 + R_1 T_2 + T_1 \quad \text{[Equation 28]}$$

Therefore, $R_2 R_3$ may be substituted as Equation 27 by the Equation 29.

$$R_2 R_3 = R_1^{-1} R_a R_b \quad \text{[Equation 29]}$$

Therefore, Equation 30 may be expressed by substituting $R_D$ for $R_1^{-1}$ Ra in the Equation 28.

$$R_D R_b - R_2 R_3 = 0 \quad \text{[Equation 30]}$$

And, $R_D R_b$ may be expressed by an Equation 31, and $R_2 R_3$ may be expressed by an Equation 32.

[Equation 31]

$$R_D R_b = \begin{bmatrix} r_{11\_D} & r_{12\_D} & r_{13\_D} \\ r_{21\_D} & r_{22\_D} & r_{23\_D} \\ r_{31\_D} & r_{32\_D} & r_{33\_D} \end{bmatrix}\begin{bmatrix} r_{11\_b} & r_{12\_b} & r_{13\_b} \\ r_{21\_b} & r_{22\_b} & r_{23\_b} \\ r_{31\_b} & r_{32\_b} & r_{33\_b} \end{bmatrix} =$$

$$\begin{bmatrix} r_{11\_D} \cdot r_{11\_b} + r_{12\_D} \cdot r_{21\_b} + r_{13\_D} \cdot r_{31\_b} & r_{11\_D} \cdot r_{12\_b} + r_{12\_D} \cdot r_{22\_b} + r_{13\_D} \cdot r_{32\_b} & r_{11\_D} \cdot r_{13\_b} + r_{12\_D} \cdot r_{23\_b} + r_{13\_D} \cdot r_{33\_b} \\ r_{21\_D} \cdot r_{11\_b} + r_{22\_D} \cdot r_{21\_b} + r_{23\_D} \cdot r_{31\_b} & r_{21\_D} \cdot r_{12\_b} + r_{22\_D} \cdot r_{22\_b} + r_{23\_D} \cdot r_{32\_b} & r_{21\_D} \cdot r_{13\_b} + r_{23\_D} \cdot r_{23\_b} + r_{23\_D} \cdot r_{33\_b} \\ r_{31\_D} \cdot r_{11\_b} + r_{32\_D} \cdot r_{21\_b} + r_{33\_D} \cdot r_{31\_b} & r_{31\_D} \cdot r_{12\_b} + r_{32\_D} \cdot r_{22\_b} + r_{33\_D} \cdot r_{32\_b} & r_{31\_D} \cdot r_{13\_b} + r_{32\_D} \cdot r_{23\_b} + r_{33\_D} \cdot r_{33\_b} \end{bmatrix}$$

[Equation 32]

$$R_2 R_3 = \begin{bmatrix} r_{11\_2} & r_{12\_2} & r_{13\_2} \\ r_{21\_2} & r_{22\_2} & r_{23\_2} \\ r_{31\_2} & r_{32\_2} & r_{33\_2} \end{bmatrix}\begin{bmatrix} r_{11\_3} & r_{12\_3} & r_{13\_3} \\ r_{21\_3} & r_{22\_3} & r_{23\_3} \\ r_{31\_3} & r_{32\_3} & r_{33\_3} \end{bmatrix} =$$

$$\begin{bmatrix} r_{11\_2} \cdot r_{11\_3} + r_{12\_2} \cdot r_{21\_3} + r_{13\_2} \cdot r_{31\_3} & r_{11\_2} \cdot r_{12\_3} + r_{12\_2} \cdot r_{22\_3} + r_{13\_2} \cdot r_{32\_3} & r_{11\_2} \cdot r_{13\_3} + r_{12\_2} \cdot r_{23\_3} + r_{13\_2} \cdot r_{33\_3} \\ r_{21\_2} \cdot r_{11\_3} + r_{22\_2} \cdot r_{21\_3} + r_{23\_2} \cdot r_{31\_3} & r_{21\_2} \cdot r_{12\_3} + r_{22\_2} \cdot r_{22\_3} + r_{23\_2} \cdot r_{32\_3} & r_{21\_2} \cdot r_{13\_3} + r_{23\_2} \cdot r_{23\_3} + r_{23\_2} \cdot r_{33\_3} \\ r_{31\_2} \cdot r_{11\_3} + r_{32\_2} \cdot r_{21\_3} + r_{33\_2} \cdot r_{31\_3} & r_{31\_2} \cdot r_{12\_3} + r_{32\_2} \cdot r_{22\_3} + r_{33\_2} \cdot r_{32\_3} & r_{31\_2} \cdot r_{13\_3} + r_{32\_2} \cdot r_{23\_3} + r_{33\_2} \cdot r_{33\_3} \end{bmatrix}$$

Therefore, the Equation 30 may be expressed by the Equation 33 by substituting $R_D R_b$ (Equation 31), and $R_2 R_3$ (Equation 32) in the Equation 30.

[Equation 33]

$$\begin{bmatrix} r_{11\_D} & 0 & 0 & r_{12\_D} & 0 & 0 & r_{13\_D} & 0 & 0 & -r_{11\_3} & -r_{21\_3} & -r_{31\_3} & 0 & 0 & 0 & 0 & 0 & 0 \\ 0 & r_{11\_D} & 0 & 0 & r_{12\_D} & 0 & 0 & r_{13\_D} & 0 & -r_{12\_3} & -r_{22\_3} & -r_{32\_3} & 0 & 0 & 0 & 0 & 0 & 0 \\ 0 & 0 & r_{11\_D} & 0 & 0 & r_{12\_D} & 0 & 0 & r_{13\_D} & -r_{13\_3} & -r_{23\_3} & -r_{33\_3} & 0 & 0 & 0 & 0 & 0 & 0 \\ r_{21\_D} & 0 & 0 & r_{22\_D} & 0 & 0 & r_{23\_D} & 0 & 0 & 0 & 0 & 0 & -r_{11\_3} & -r_{21\_3} & -r_{31\_3} & 0 & 0 & 0 \\ 0 & r_{21\_D} & 0 & 0 & r_{22\_D} & 0 & 0 & r_{23\_D} & 0 & 0 & 0 & 0 & -r_{12\_3} & -r_{22\_3} & -r_{32\_3} & 0 & 0 & 0 \\ 0 & 0 & r_{21\_D} & 0 & 0 & r_{22\_D} & 0 & 0 & r_{23\_D} & 0 & 0 & 0 & -r_{13\_3} & -r_{23\_3} & -r_{33\_3} & 0 & 0 & 0 \\ r_{31\_D} & 0 & 0 & r_{32\_D} & 0 & 0 & r_{33\_D} & 0 & 0 & 0 & 0 & 0 & 0 & 0 & 0 & -r_{11\_3} & -r_{21\_3} & -r_{31\_3} \\ 0 & r_{31\_D} & 0 & 0 & r_{32\_D} & 0 & 0 & r_{33\_D} & 0 & 0 & 0 & 0 & 0 & 0 & 0 & -r_{12\_3} & -r_{22\_3} & -r_{32\_3} \\ 0 & 0 & r_{31\_D} & 0 & 0 & r_{32\_D} & 0 & 0 & r_{33\_D} & 0 & 0 & 0 & 0 & 0 & 0 & -r_{13\_3} & -r_{23\_3} & -r_{33\_3} \end{bmatrix} \begin{bmatrix} r_{11\_b} \\ r_{12\_b} \\ r_{13\_b} \\ r_{21\_b} \\ r_{22\_b} \\ r_{23\_b} \\ r_{31\_b} \\ r_{32\_b} \\ r_{33\_b} \\ r_{11\_2} \\ r_{12\_2} \\ r_{13\_2} \\ r_{21\_2} \\ r_{22\_2} \\ r_{23\_2} \\ r_{31\_2} \\ r_{32\_2} \\ r_{33\_2} \end{bmatrix} = \begin{bmatrix} 0 \\ 0 \\ 0 \\ 0 \\ 0 \\ 0 \\ 0 \\ 0 \\ 0 \end{bmatrix}$$

The unknown parameters, r11, r12_b, r13_b, r21_b, r22_b, r23_b, r31_b, r32_b, r33_b, r11_2, r12_2, r13_2, r21_2, r22_2, r23_2, r31_2, r32_2, r33_2, to be calculated are eighteen, and therefore, at least one of the optical tracker 210, the camera 220, and the pattern board 230 may be moved at least once or at least one of the camera 220 and the pattern board 230 may be moved at least once to solve the Equations since nine Equations are generated from one configuration.

Therefore, spatial coordinates of the first and second markers 240 and 250 are changed at least once, at least two spatial coordinates of the first and second markers 240 and 250 from the spatial coordinate of the optical tracker 210 and at least two spatial coordinates of the origin of the pattern board 230 from the spatial coordinate of the optical center of the camera 220 are stored in the processor, and the spatial coordinate of the optical center of the camera 220 is adjusted by the processor by calculating the spatial coordinate of the optical center of the camera 220 from the first marker 240 and the spatial coordinate of the origin of the pattern board 220 from the second marker 250.

As described above, a method of registering a camera of surgical navigation system for an augmented reality comprises attaching a second marker 250 on a pattern board 230, changing at least one time spatial coordinates of the first and second markers 240 and 250, and adjusting the spatial coordinate of the optical center of the camera 220 from a spatial coordinate of a second marker 250

The detailed description of the present invention is described with regard to the preferable embodiment of the present invention, however, a person skilled in the art may amend or modify the present invention within the spirit or scope in the following claim of the present invention.

What is claimed is:

1. A method of registering a camera of a surgical navigation system for an augmented reality, comprising:
   a first step of finding, by a processor, coordinate relations between spatial coordinates of first and second markers and a spatial coordinate of an optical tracker, wherein the first and second markers are attached on the camera and the pattern board, respectively, and tracked by the optical tracker, calculating a coordinate relation between a spatial coordinate of an origin of a pattern board and a spatial coordinate of an optical center of a camera, and storing the coordinate relations in the processor, wherein the spatial coordinates of the first and second markers have been changed multiple times; and a second step of adjusting, by the processor, the spatial coordinate of the optical center of the camera by using the coordinate relations between the spatial coordinates of the first and second markers and the spatial coordinate of the optical tracker, which are stored in the processor, and the coordinate relation between the spatial coordinate of the origin of the pattern board and the spatial coordinate of the optical center of the camera, which is stored in the processor, and storing the adjusted spatial coordinate of the optical center of the camera in the processor to register the camera of the surgical navigation system.

2. The method of claim 1, wherein the second marker is attached on a portion of the pattern board on which a pattern is formed.

3. The method of claim 1, wherein the second marker is attached on a portion of the pattern board on which a pattern is not formed.

4. The method of claim 1, wherein a chess pattern or a circular pattern is formed on the pattern board.

5. The method of claim 1, wherein the first step comprises:

finding, by the processor, the coordinate relations between the spatial coordinates of the first and second markers and the spatial coordinate of the optical tracker by tracking the first and second markers by the optical tracker;

calculating, by the processor, the coordinate relation between the spatial coordinate of the origin of the pattern board and the spatial coordinate of the optical center of the camera by using an image of the pattern board obtained by the camera; and changing the coordinate relations between spatial coordinates of the first and second markers and the spatial coordinate of the optical tracker by multiple times and performing, for each time, the step of finding the coordinate relations between the spatial coordinates of the first and second markers and the spatial coordinate of the optical tracker and the step of calculating the coordinate relation between the spatial coordinate of the origin of the pattern board and the spatial coordinate of the optical center of the camera, so as to find respective coordinate relations between the spatial coordinates of the first and second markers and the spatial coordinate of the optical tracker and respective coordinate relation between the spatial coordinate of the origin of the pattern board and the spatial coordinate of the optical center of the camera.

6. The method of claim 5, wherein calculating the spatial coordinate of the origin of the pattern board comprises:

capturing, by the camera, the image of the pattern board;

transmitting the captured image of the pattern board obtained from the camera to the processor; and calculating, by the processor, the coordinate relations between the spatial coordinate of the origin of the pattern board and the spatial coordinate of the optical center of the camera by using the captured image of the pattern board.

7. The method of claim 1, wherein the spatial coordinates of the first and second markers, which are tracked by the optical tracker, are changed by moving at least one of the optical tracker, the pattern board, and the camera, by at least four times.

8. The method of claim 1, wherein the second step comprises:

calculating, by the processor, the coordinate relation between the spatial coordinate of the optical center of the camera and the first marker and the coordinate relation between the spatial coordinate of the origin of the pattern board and the second marker by using the coordinate relations between the spatial coordinates of the first and second markers and the spatial coordinate of the optical tracker and the coordinate relation between the spatial coordinate of the origin of the pattern board and the spatial coordinate of the optical center of the camera, which are stored in the processor;

adjusting, by the processor, the spatial coordinate of the optical center of the camera by using the coordinate relation between the spatial coordinate of the optical center of the camera and the first marker and the coordinate relation between the spatial coordinate of the origin of the pattern board and the second marker, which are calculated by the processor; and storing the adjusted spatial coordinate of the optical center of the camera, which is determined by the processor, in the processor.

9. The method of claim 8, wherein the coordinate relation between spatial coordinate of the optical center of the camera and the first marker is determined by calculating, by the processor, the coordinate relation between the spatial coordinate of the optical center of the camera and the spatial coordinate of the first marker in a condition that a coordinate relation between a spatial coordinate of the optical center of the camera and the optical tracker via the first marker is identical to a coordinate relation between a spatial coordinate of the optical center of the camera and the optical tracker via the second marker and the origin of the pattern board.

10. The method of claim 1, wherein the spatial coordinates of the first and second markers, which are tracked by the optical tracker, are changed by moving at least once a position of at least one of the optical camera, the pattern board, and the camera.

11. A method of registering a camera of a surgical navigation system for an augmented reality, comprising:

a first step of finding, by a processor, coordinate relations between spatial coordinates of first and second markers and a spatial coordinate of an optical tracker, wherein the first and second markers are attached on the camera and the pattern board, respectively, and tracked by the optical tracker, calculating a coordinate relation between a spatial coordinate of an origin of a pattern board and a spatial coordinate of an optical center of a camera, and storing the coordinate relations in the processor, wherein the coordinate relations between the spatial coordinates of the first and second markers and the spatial coordinate of the optical tracker have been changed multiple times; and a second step of adjusting, by the processor, the spatial coordinate of the optical center of the camera by using the coordinate relations between the spatial coordinates of the first and second markers and the spatial coordinate of the optical tracker, which are stored in the processor, and the coordinate relation between the spatial coordinate of the origin of the pattern board and the spatial coordinate of the optical center of the camera, which is stored in the processor, and storing the adjusted spatial coordinate of the optical center of the camera and the first marker in the processor to register the camera of the surgical navigation system.

* * * * *